United States Patent [19]

Lacey

[11] Patent Number: 4,759,767
[45] Date of Patent: Jul. 26, 1988

[54] PROSTHESIS FOR TIBIAL COMPONENT OF KNEE JOINT

[75] Inventor: James A. Lacey, Winter Park, Fla.

[73] Assignee: Dow Corning Wright Corporation, Arlington, Tenn.

[21] Appl. No.: 83,326

[22] Filed: Aug. 10, 1987

[51] Int. Cl.⁴ .................................................. A61F 2/38
[52] U.S. Cl. ........................................................ 623/20
[58] Field of Search ...................................... 623/16–23

[56] References Cited

U.S. PATENT DOCUMENTS

| | | | |
|---|---|---|---|
| 3,728,742 | 4/1973 | Averill et al. | 623/20 |
| 3,869,730 | 3/1975 | Skobel | 623/19 |
| 4,016,606 | 4/1977 | Murray et al. | 623/20 |

FOREIGN PATENT DOCUMENTS

| | | | |
|---|---|---|---|
| 3205527 | 8/1983 | Fed. Rep. of Germany | 623/22 |
| 0719625 | 3/1980 | U.S.S.R. | 623/20 |
| 0757159 | 8/1980 | U.S.S.R. | 623/20 |

OTHER PUBLICATIONS

Zimmer "Here's a Good Skate" J of Bone & Joint Surgery, vol. 53-A, No. 5, Jul. 1971.

Primary Examiner—Richard J. Apley
Assistant Examiner—David J. Isabella
Attorney, Agent, or Firm—Allan O. Maki

[57] ABSTRACT

A prosthesis for replacing the proximal end of a tibia, installable without bone cement which includes a tibial plateau portion adapted to receive an articulation insert. Integral with the underside of the plateau is an intermedullary fixation stem to which is attached a medial-lateral fin. Attached to each end of the fin is a transverse fin which provides a dual "T" configuration, which provides superior anchoring of the prosthesis.

5 Claims, 2 Drawing Sheets

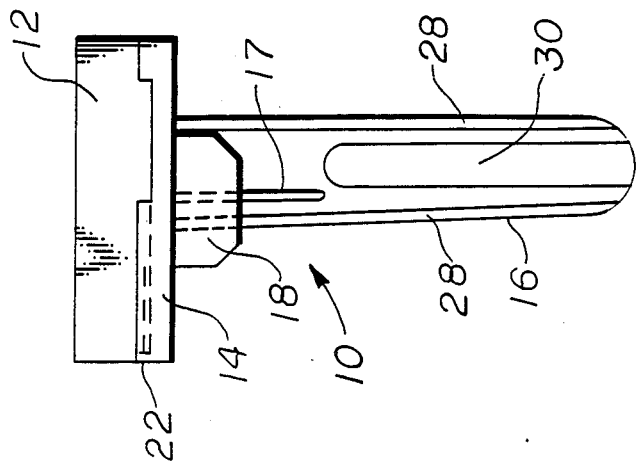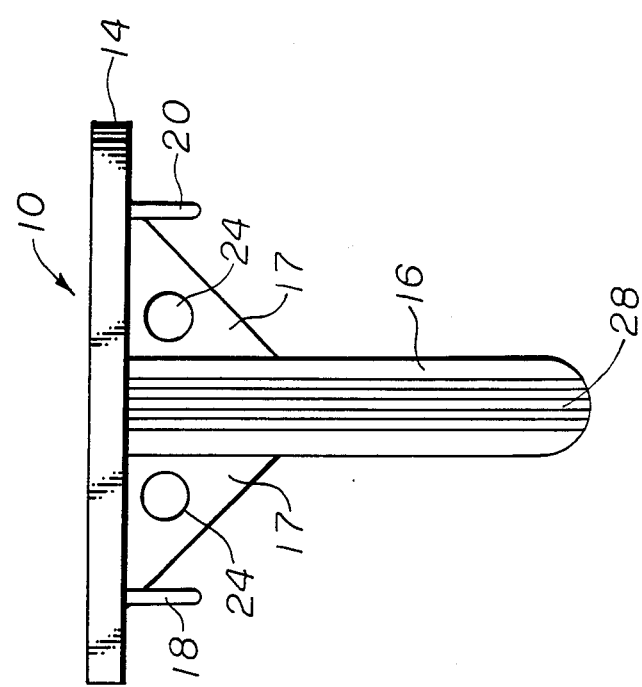

PROSTHESIS FOR TIBIAL COMPONENT OF KNEE JOINT

BACKGROUND OF THE INVENTION

The knee is generally regarded as being the most inherently unstable of the joints of the human body, due in part to the complex inter-related types of motions to which the several knee elements are subjected during ambulatory movements of the body. Various prostheses have hithertofore been proposed in attempts to approximate, through an artificial joint, the natural action of the human knee. Advanced conditions of disease or serious traumatic injury of the knee joint complicate surgical repair and efforts to simulate the natural knee motion through use of a prosthesis.

Several types of prostheses, each having advantages and disadvantages have been employed. One type currently in use is the hinged type such as described in my U.S. Pat. No. 4,262,368. Other prostheses are employed in which the femoral and tibial components are unconnected. Most of the latter systems rely on the use of bone cement to assist in anchoring the prosthesis to the resected femur.

U.S. Pat. No. 4,355,429 discloses a knee joint prosthesis which is secured without cement. Anchoring is accomplished by utilizing pins inserted into slightly undersize holes drilled into the bone. There is no disclosure of the use of dual T-shaped fins or flanges integral with the implant which serves to stably, mechanically anchor the device.

U.S. Pat. No. 4,217,666 discloses a tibial prosthesis component which uses an intermedullary stem of U-shaped configuration in order to retain the cruciate ligament. It is further stated that the stem may be texturized with grooves, perforations or ridges. The prosthesis is, however, disclosed as being implanted with the aid of bone cement.

The general objects of the present invention are to provide an improved tibial prothesis designed for insertion without cement. The implants of the present invention provide immediate mechanical fixation to the bone by the use of a combination of an intermedullary anchoring stem and medial-lateral fin type elements having intersecting fin type elements at each end which are designed to be implanted in a resected tibia into which slightly undersized apertures or slots have been osteotomized. The fins create a dual T-pattern that resists torsional forces. Such configuration and placement of the fins has been found to provide stable anchoring of the prosthesis wihout the use of bone cement.

SUMMARY OF THE INVENTION

The invention provides a tibial implant posthesis designed to replace the articulating proximal surfaces of the human tibia which is implanted without the use of bone cement, and which provides improved stability and resistance to tilting and torsional forces. The prosthesis of this invention includes a unitary, one-piece base portion adapted to be used in conjunction with a removable resinous polymeric tibial plateau articulation insert. The base portion is provided with an intergral stem and medial-lateral fins of a dual "T" shaped configuration so that it can be mechanically connected to the resected tibia by downward driving implantation. The underside of the plateau base may be provided with a "waffled" design or similar texture which promotes bone ingrowth.

DRAWINGS

Preferred embodiments of the invention will be set forth by way of example in the following detailed description and appended drawings, wherein:

FIG. 1 is an elevational view of the tibial prosthesis of the present invention;

FIG. 3 is a lateral view of the prosthesis showing, in place, an articulating surface insert which interacts with the condylar surfaces of a femoral prosthesis; and, FIG. 4 is a bottom view of the preferred embodiment of the prosthesis.

DETAILED DESCRIPTION

Figure 4:
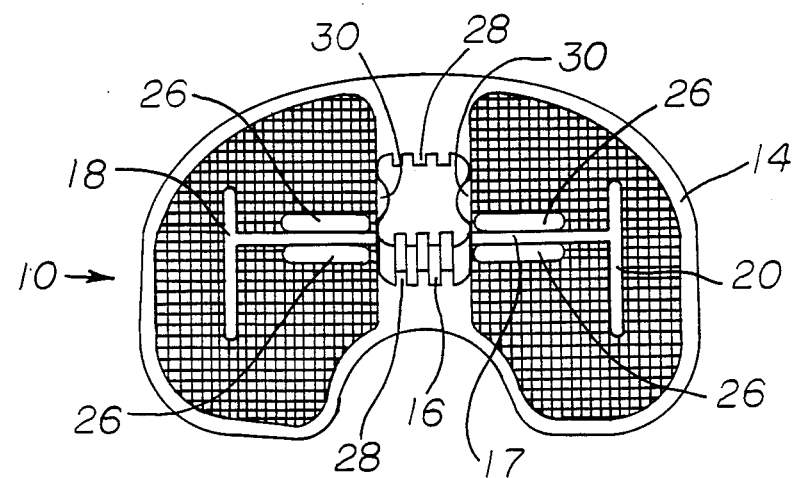
Figure 2:
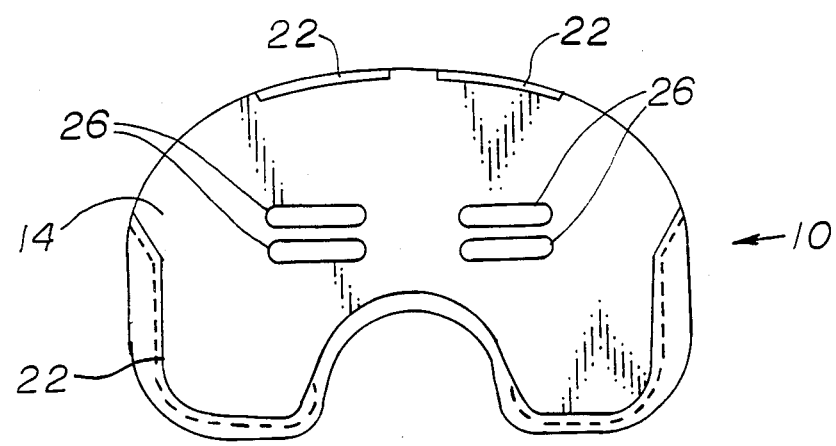
FIG. 2 is a top view of said prosthesis.

Referring specifically to the drawings, there is seen a prosthesis identified generally by numeral 10, which in conjunction with a replaceable plateau insert 12 is designed to replace the articulating surfaces of a human tibia. The prosthesis or implant is preferably made of titanium, cobalt-chromium alloys or similar biocompatible and non-corroding materials. The base portion 14 has integral therewith a downwardly extending stem portion 16, a medial-lateral fin element 17 and transversely oriented fin members 18 and 20. As best seen in FIG. 1, the medial-lateral fin members 17 are preferably of a greater width adjacent to the stem and taper to a narrower width laterally on each side of the stem. This allows for shallower cuts into the lateral edges of the resected tibia. Great stability is nonetheless achieved by providing transverse fins 18 and 20 of a length such that they traverse an major portion of the anterior-posterior dimension of the bone at the point of implantation.

Insert 12 can be made of any biocompatible hard synthetic polymeric material which is suitable for implantation within the human body and has physical properties which permit it to be affixed to the prosthesis as well as sufficient wear resistance to permit its use as an articulating surface for a knee prosthesis. The preferred material is ultrahigh molecular weight polyethylene which is commercially available and conventionally used for tibial prosthesis articulating surfaces. Another example is carbon fiber-reinforced polyethylene. The preferred method for attachment of the insert is by the use of undercut flanges extending upward from the peripheries of the plateau which coact with appropriate grooves 22 in the lower periphery of the insert. Other means of attachment are known, however, and will be apparent to those skilled in the art.

Holes 24 are provided in the medial-lateral fin 17 to provide for bone ingrowth after implantation of the prosthesis. Osteotome slots 26 are provided to allow for easier removal of the implant should the need ever arise. As seen in FIG. 4, the underside of the base portion 14 is provided with a waffle patterned texture, in the preferred embodiment, in order to promote further bone ingrowth.

Stem 16 is designed to be driven into a slightly undersized cavity cut into the resected proximal surface of the tibia. Grooves 28 are preferably provided on the anterior and posterior surfaces of stem 16, as are elongated recesses 30 on the sides thereof. Grooves or flutes 28 along with the illustrated geometry of stem 16 prevents tilting of the implant due to eccentric loading and also prevents anterior lift-off.

It is to be understood that the foregoing embodiments are to be considered illustrative of the invention. Various modifications, changes or alterations of the invention disclosed herein may be evident to those skilled in the art and thus the invention disclosed herein is not intended to be limited by the description hereinabove but rather, is intended to be limited only by the appended claims.

What is claimed is:

1. A prosthetic device for replacing at least a portion of the proximal end of a tibia comprising a unitary, one-piece device adapted to be connected to the proximal end of a resected tibia without cement and to replace the articulating surfaces thereof, said prosthesis including
    (A) a tibial plateau portion having means to receive a artculation insert,
    (B) a intermedullary fixation stem attached to the underside of said plateau portion,
    (C) a medial-lateral fin having one side attached to the underside of said plateau portion and an adjacent side attached to said stem and extending outwardly in a medial and lateral direction from each side of said stem,
    (D) a terminal fin member attached to each end of said medial-lateral fin and positioned transverseley relative thereto and extending from said plateau portion distally therefrom.

2. A tibial prosthesis according to claim 1 wherein said prosthesis is constructed from a metal or metal alloy.

3. A tibial prosthesis according to claim 1 wherein said stem is provided with elongated vertical flutes on the anterior and posterior surfaces thereof.

4. A tibial prosthesis according to claim 1 wherein said medial-lateral fin is provided with holes extending therethrough.

5. A tibial prosthesis according to claim 1 wherein the under surface of said plateau portion is provided with a waffle type texture to promote bone ingrowth.

* * * * *